Figure 1:
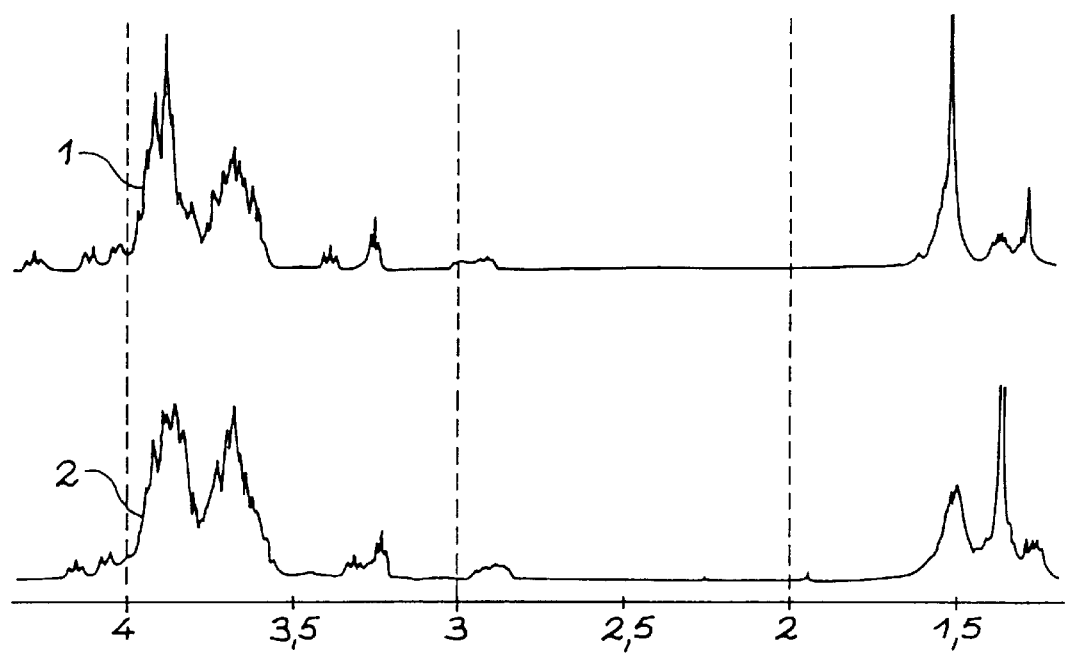

United States Patent [19]

Djedaini-Pilard et al.

[11] Patent Number: 5,821,349

[45] Date of Patent: Oct. 13, 1998

[54] DERIVATIVES OF CYCLODEXTRINS, THEIR PREPARATION AND THEIR USE FOR INCORPORATING HYDROPHOBIC MOLECULES INTO ORGANIZED SURFACTANT SYSTEMS

[75] Inventors: Florence Djedaini-Pilard, Etampes; Jing Lin, Savigny-sur Orge; Bruno Perly, La Verriere, all of France

[73] Assignee: Commissariat a l'Energie Atomique, Paris, France

[21] Appl. No.: 659,824

[22] Filed: Jun. 7, 1996

[30] Foreign Application Priority Data

Jun. 29, 1995 [FR] France .................................. 95 07841

[51] Int. Cl.$^6$ ........................ C08B 37/16; A61K 31/715; A01N 43/04
[52] U.S. Cl. .............................. 536/103; 536/124; 514/58
[58] Field of Search ...................................... 536/103, 124; 514/58

[56] References Cited

FOREIGN PATENT DOCUMENTS

WO 90/02141  3/1990  WIPO.
WO 95/15746  6/1995  WIPO.

OTHER PUBLICATIONS

Chemical Abstracts, vol. 109, No. 3, issued 18 Jul. 1988, Matsui et al, Preparation of cyclodextrin containing polymer membranes for optical resolution of amino acids, p. 663, column 1 and 2, abstract No. 23379p, Jpn. Kokai Tokkyo Koho 87/258,702.

Chemical Abstracts, vol. 91, No. 16, issued 15 Oct. 1979, Tabushi et al, "Metal complexes of cyclodextrin derivatives of polystyrene"p. 31, column 1 and 2, abstract No. 124390a, Jpn. Kokai Tokkyo Koho 79/61,290.

Chemical Abstract, vol. 90, No. 5, issued 18 Jan. 1979, Tabushi et al, "Cyclodextrin metal complexes", p. 5/8, column 2m abstract No. 39197c, Jpn. Kokai Tokkyo Koho 78/102,986.

Primary Examiner—John Kight
Assistant Examiner—Everett White
Attorney, Agent, or Firm—Oblon, Spivak, McClelland, Maier, & Neustadt, P.C.

[57] ABSTRACT

The invention relates to derivatives of cyclodextrins, their preparation and their use for incorporating hydrophobic molecules into organized surfactant systems. These derivatives of cyclodextrins are in accordance with the formula:

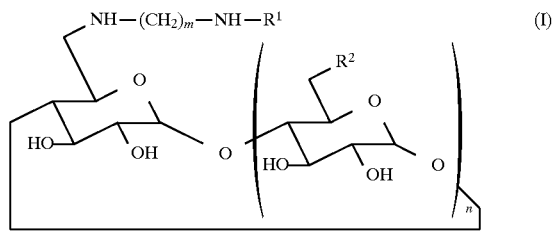

in which $R^1$ represents a group protecting an amine function, the $R^2$, which can be the same or different, represent OH or $NH-CH_2m-NHR^1$, m being an integer from 2 to 18 and n is equal to 5, 6 or 7.

23 Claims, 2 Drawing Sheets

DERIVATIVES OF CYCLODEXTRINS, THEIR PREPARATION AND THEIR USE FOR INCORPORATING HYDROPHOBIC MOLECULES INTO ORGANIZED SURFACTANT SYSTEMS

DESCRIPTION

The present invention relates to novel derivatives of cyclodextrins, more particularly usable for the incorporation into aqueous media of hydrophobic chemical compounds such as pharmaceutically active molecules.

More specifically, it relates to amphiphilic derivatives of cyclodextrins permitting on the one hand the inclusion of hydrophobic molecules into cyclodextrin for forming an inclusion complex and on the other the incorporation of such complexes into systems of organized surfactants such as small phospholipid vesicles.

This incorporation is intended to permit the transport of the hydrophobic molecule, e.g. an active principle, in particular by the transmembrane, e.g. transdermal route.

Cyclodextrins or cyclomaltoologosaccharides are compounds having a natural origin formed by the linking of 6, 7 or 8 glucose units linked in $\alpha 1 \rightarrow 4$. Numerous works have shown that these cyclodextrins could form inclusion complexes with hydrophobic molecules and thus permit the solubilization of these molecules in aqueous media. Numerous applications have been proposed for taking advantage of this phenomenon, particularly in the pharmaceutical field, as is described by D. Duchêne in the work entitled "Cyclodextrins and their industrial uses", chapter 6, pp 213 to 257, Editions de Sante, 1987. Pharmaceutical compositions using cyclodextrins have been marketed in Japan, Italy and more recently France, e.g. by Pierre Fabre Medicament for Brexin$^{(R)}$ which is an inclusion complex of Piroxicam in β-cyclodextrin.

Among the usable cyclodextrins, β-cyclodextrin, which has 7 glucose units, is the most suitable with regards to the size of its cavity and it is the least costly of the three. Numerous chemical modifications of β-cyclodextrin have been described with a view to rendering it amphiphilic so as to be able to incorporate it in organized systems.

Thus, L. Jullien et al have described in J. Chem. Soc. Perkin Trans 2, 1993, pp 1011–1020, β-cyclodextrin derivatives having aliphatic chains in the primary and secondary positions, with a view to incorporating these derivatives of cyclodextrins in phosphatidylcholine vesicles. These derivatives are amphiphilic and can consequently be incorporated into the vesicles, but the internal cavity of the cyclodextrin is no longer accessible due to the large steric space requirements of aliphatic chains. Consequently these derivatives are unable to include hydrophobic molecules, particularly active principle molecules.

N. Bellanger and B. Perly have described in J. Mol. Struc., 1992, 293,pp 215–226, amino derivatives of cyclodextrins having a single aliphatic chain on the amino group of mono-6-deoxy-6-amino-cyclodextrin, obtained by the reaction of the amino derivative with a carboxylic acid. Although these derivatives only incorporate a single aliphatic chain, they suffer from the disadvantage of leading to an auto-inclusion of the aliphatic chain in the cyclodextrin, which does not permit the incorporation of small vesicles of phospholipids or the inclusion of hydrophobic molecules in the internal cavity of the cyclodextrin.

The present invention specifically relates to other derivatives of cyclodextrins, which have one or more aliphatic chains giving them amphiphilic properties, without leading to the auto-inclusion phenomenon of the chain or chains in the cyclodextrin. Thus, from said derivatives, it is possible to obtain inclusion complexes containing a hydrophobic molecule and the incorporation of these complexes into vesicles of phospholipids.

According to the invention, the cyclodextrin derivative complies with the formula:

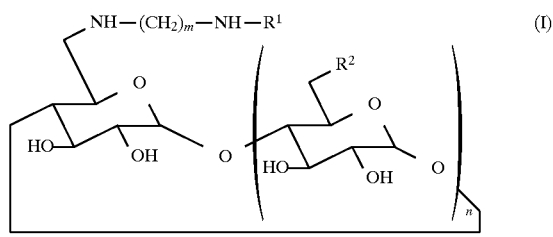

in which $R^1$ represents a group protecting an amine function, the $R^2$ can be the same or different and represent OH or NH—$(CH_2)_m$—$NHR^1$, m is an integer from 2 to 18 and n is equal to 5, 6 or 7.

In this derivative, amphiphilic properties are obtained due to the grafting of at least one aliphatic chain $(CH_2)_m$—NH—$R^1$, which does not give rise to the auto-inclusion phenomenon when the cyclodextrin derivative is in the aqueous medium. Thus, it is possible to obtain from said derivative an inclusion complex by the incorporation of a hydrophobic molecule into the internal cavity of the cyclodextrin and said inclusion complex can be incorporated into small vesicles of phospholipids.

Preferably the cyclodextrin derivative has a single aliphatic chain, all the $R^2$ representing OH.

In the cyclodextrin derivative according to the invention, the $R^1$ group protects the amine function $NH_2$. In order to fulfil this function, $R^1$ can represent the nitrophenyl sulphenyl group, the fluoren-9-yl methoxycarbonyl group or a group of formula $COOR^3$, in which $R^3$ can be a straight or branched alkyl group or an aryl group, optionally in substituted form.

When use is made of an alkyl group, the latter generally has 4 to 18 carbon atoms and it is preferably branched. The aryl group can e.g. be the benzyl group.

Advantageously $R^3$ represents the tert.-butyl group.

The cyclodextrin derivatives according to the invention can be derivatives of α, β or γ-cyclodextrin. Preference is given to the use of β-cyclo-dextrin derivatives, which corresponds in formula (I) to the case where n is 6.

The aliphatic chain of the cyclodextrin derivative according to the invention can have between the two amino groups 2 to 18 carbon atoms. Good results are in particular obtained when m is between 6 and 12, e.g. 6.

The cyclodextrin derivatives according to the invention can be prepared by conventional processes. Thus, it is possible to prepare the derivatives of formula (I) in which all the $R^2$ represent OH, from the corresponding tosylated or naphthosulphonylated derivatives.

Thus, the invention also relates to a process for the preparation of the cyclodextrin derivative according to formula (I), in which all the $R^2$ represent OH and which comprises the following stages:

a) reacting a cyclodextrin derivative of formula:

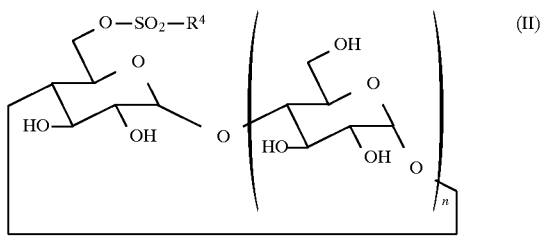

in which $R^3$ is a tosyl or naphthosulphonyl group, and n is equal to 5, 6 or 7, with a diaminoalkane of formula $NH_2$—$(CH_2)_m$—$NH_2$ in which m has the meaning given hereinbefore, to obtain a cyclodextrin derivative of formula:

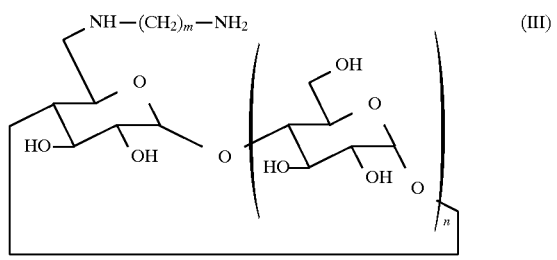

in which n and m are as defined hereinbefore and b) reacting the derivative of formula (III) with a reagent having the protecting group $R^1$ so as to obtain the cyclodextrin derivative of formula (I).

In stage a) of this process, the cyclodextrin derivative of formula (II) is reacted with the desired diaminoalkane in an organic solvent such as dimethyl formamide (DMF) in the presence of a tertiary amine such as diisopropyl ethyl amine, in order to accelerate the reaction.

It is possible to separate the thus obtained derivative of formula (III) from the reaction medium by evaporation of the solvent and by precipitation. The precipitation stage can be repeated, so as to purify the derivative by ion exchange chromatography, in order to eliminate the natural cyclodextrin which has not reacted. Precipitation can take place by adding the concentrated reaction mixture to an organic solvent such as acetone and then separating the precipitate formed by filtration or centrifuging. It is thus possible to eliminate all the derivatives of the sulphonic acid, as well as the diamine present in excess and the diisopropyl ethyl amine, all of which are soluble in an organic solvent such as acetone.

In stage b), the derivative of formula (III) is reacted with the desired reagent, e.g. a ditert. butyl dicarbonate, when $R^1$ represents the tert.butyl oxycarbonyl group, in an organic solvent such as DMF.

When $R^1$ represents a nitrophenyl sulphenyl group, the reagent used can be nitrophenyl sulphenyl chloride.

When $R^1$ represents the fluoren-9-yl-methoxycarbonyl group, the reagent used can be fluoren-9-yl-methoxy succinimidyl carbonate.

When $R^1$ is the benzyloxycarbonyl group or a group of formula —$COOR^3$, it is possible to use for this reaction the benzyloxycarbonyl chloride or azide.

The cyclodextrin derivative of formula (I) obtained in this way can be purified by successive precipitations in an organic solvent such as acetone.

The tosylated or naphthosulphonylated derivative of formula (II) used as the starting product in the process according to the invention can be prepared by the reaction of p-toluene sulphenyl chloride or naphthosulphenyl chloride on the corresponding cyclodextrin in an aqueous medium.

When it is desired to prepare a cyclodextrin derivative corresponding to formula (I) given hereinbefore, in which one or more $R^2$ represent NH—$(CH_2)_m$—$NHR^1$, it is possible to start form the corresponding halogen, bromine or iodine derivatives, which are reacted with the diaminolkane of formula $NH_2$—$(CH_2)_mNH_2$ and then, as hereinbefore, a reaction is performed with a view to protecting the amine groups of the cyclodextrin derivative by the desired protecting groups.

The invention also relates to the inclusion complexes of the cyclodextrin derivative of formula (I) with a hydrophobic chemical compound such as a pharmaceutically active molecule.

The hydrophobic chemical compounds which can be included in the cyclodextrin derivative according to the invention can be of different types. Examples of such compounds are cosmetic products, vitamins, pharmaceutically active molecules such as those described by D. Duchene in the aforementioned work entitled "Cyclodextrins and their industrial uses".

Preferably, in the invention, the hydrophobic chemical compound is a pharmaceutically active molecule.

Examples of such molecules are aromatic compounds from the family of anthracyclins.

As indicated hereinbefore, the cyclodextrin derivatives according to the invention are particularly interesting with a view to their incorporation, particularly in the form of inclusion complexes containing hydrophobic molecules, into organized systems of surfactants.

The invention also relates to an organized surfactant system incorporating a cyclodextrin derivative or an inclusion complex of said derivative according to the invention.

The surfactants able to form such organized systems can be of different types. Reference can e.g. be made to phospholipids in accordance with the following general formula:

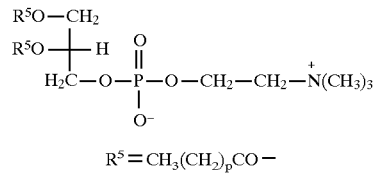

$$R^5 = CH_3(CH_2)_pCO—$$

in which $R^5$ represents $CH_3(CH_2)_pCO$-with p being an integer between 6 and 18.

These phospholipids are able to form small unilamellar vesicles. This is in particular the case with dimyristodylphosphatidylcholine (DMPC), which is in accordance with the above formula with p =12.

To incorporate the inclusion complex in the organized surfactant system, it is possible to dissolve the complex in water, then add the surfactant and then carry out a sonication.

Figure 2:
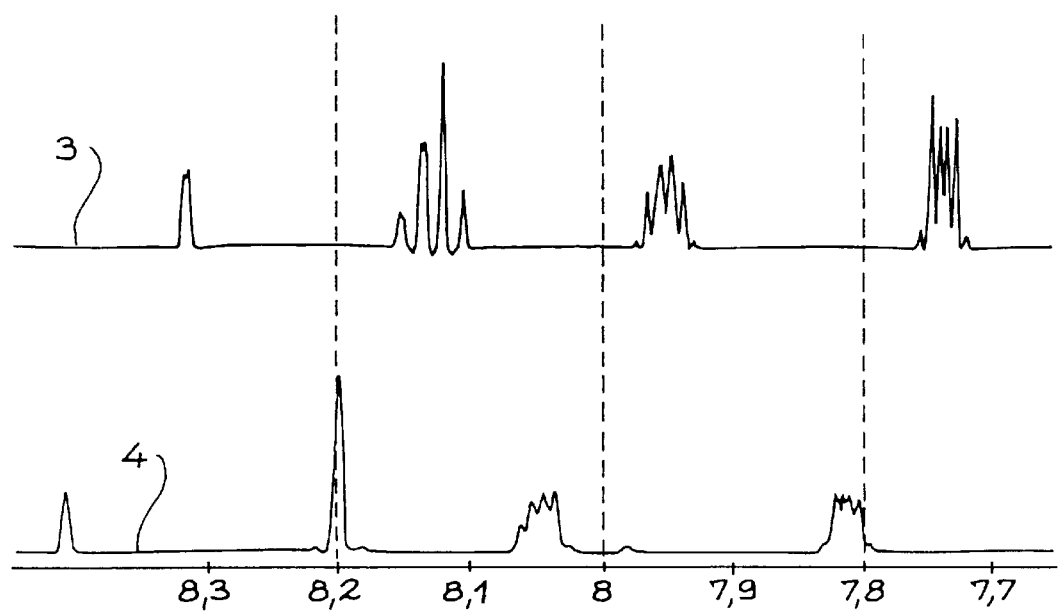
Figure 3:
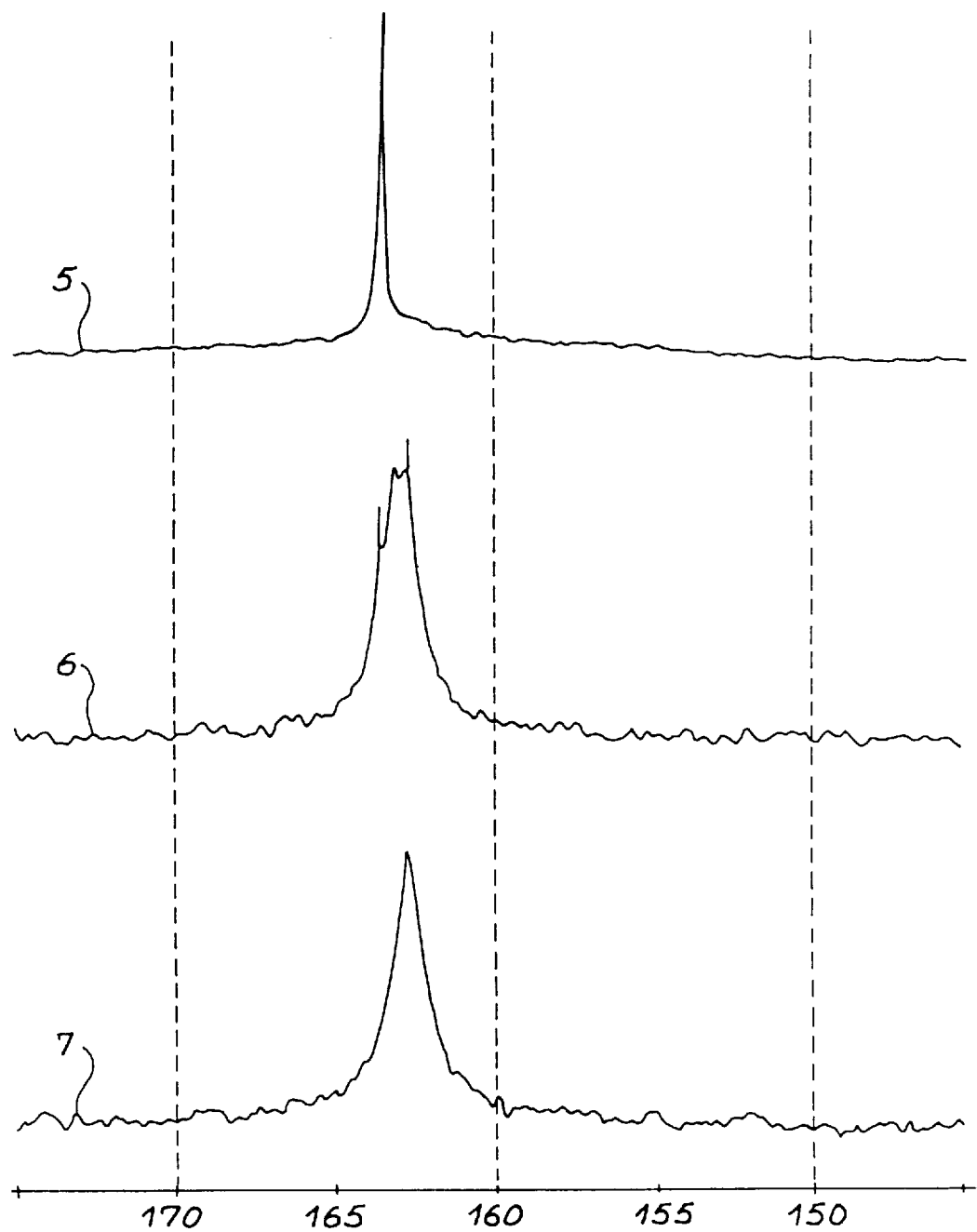

Other features and advantages of the invention can be gathered from the following illustrative and non-limitative examples with reference to FIGS. 1 to 3.

FIGS. 1 and 2 illustrate the nuclear magnetic resonance spectra of the proton of the cyclodextrin derivative obtained in example 1 (spectrum 1), the inclusion complex obtained in example 2 (spectra 2 and 4) and the ASANA alone (spectrum 3).

FIG. 3 illustrated the nuclear magnetic resonance spectra of $^{31}$ P of the inclusion complex of the invention in DMPC (spectrum 5), DMPC with the cyclodextrin derivative of example 1 (spectrum 6) and DMPC alone (spectrum 7).

EXAMPLE 1

Preparation of mon-6-deoxy-6 -N-Boc-diaminohexane-cyclomaltobeptaose a) Preparation of mono-6-deoxy-6-p-toluene sulphonyl-cyclomaltoheptaose 60 g of cyclomaltoheptaose (52.8 mmole) are suspended in 500 ml of distilled water. Dropwise additional takes place of 6.57 g (164 mmole) of caustic soda dissolved in 20 ml of water over 5 minutes, accompanied by strong magnetic stirring. To the clear solution obtained are added 10.08 g (52.9 mmole) of p-toluene sulphonyl chloride in 30 ml of acetonitrile in dropwise manner over 10 minutes. After stirring for 2 hours at ambient temperature, the precipitate formed is eliminated by filtration and the filtrate is kept for 48 hours at 4° C. The precipitate is isolated by filtration in vacuo, washed with 50 ml of ice water and recrystallized immediately in boiling water. After one night at 4° C., the precipitate is filtered and dried in vacuo at 30° C. This gives 7.5 g (12%) of a pure compound in accordance with specifications.

b) Synthesis of mono-6-deoxy-6-diamino-hexane-cyclomaltoheptaose

Into a 250 ml flask, surmounted by a condenser, are introduced 450 mg (3.87 mmole) of diaminohexane dissolved in 15 ml of DMF. Dropwise addition takes place of 400 µl (2.33 mmole) of diisopropyl ethyl amine and stirring is continued for 10 minutes. 1 g (0.776 mmole) of the mono-6-deoxy-6-p-toluene sulphonyl-cyclomaltoheptaose obtained previously and dissolved in 10 ml of DMF is added dropwise to the preceding solution. The reaction mixture is kept for 3 days under stirring at 75° C. The solvent is eliminated under reduced pressure at 40° C. The residual oil is taken up by 5 ml of water and then treated with 150 ml of acetone. After one night at 4° C., the precipitate is isolated, washed with acetone and dried in vacuo at 30° C. This gives 700 mg (73%) of mono-6-deoxy-6-diamino -hexane-cyclomaltoheptaose. The aminocyclodextrin obtained still contains a small amount of unmodified cyclodextrin resulting from the tosylation stage. The latter is easily eliminated by ion exchange resin chromatography in the following way. A solution of mono-6-deoxy-6-diamino-hexane-cyclomaltoheptaose (700 mg) in 10 ml of water is applied to a column containing 70 ml of Lewatit SP 1080 resin in form $H^+$(Merck) suspended in water. After washing with 200 ml of water, the mono-$^6$-deoxy-$^6$-diamino-hexane-cyclomaltoheptaose is eluted by an aqueous 6% ammonia solution. 200 ml of the basic eluate are collected and concentrated in vacuo at 30° C. The final traces of ammonia are eliminated by evaporation in vacuo in the presence of 20 ml of water. The residue is taken up in a minimum of water and is precipitated by 80 ml of acetone, kept at 4° C. for one night, isolated by filtration, washed with acetone and dried in vacuo at 30° C. This gives 580 mg of the end compound completely free from the initial cyclodextrin.

MS : m/z =1233 [M+H]$^+$(M =1232 calc for $C_{48}N_2O_{34}H_v$);
RMN ($^{13}$C, 125 MHz, d6-DMSO):106 ppm(C-1), 88 and 85.5 ppm(C-4) 77–74.5 ppm (C-2, C-3 and C-5), 63.8 ppm(C-6), 54 ppm(—NH—$CH_2$ and $CH_2$—$NH_2$), 33.6–30.5 ppm(4, $CH_2$).

c) Synthesis of mono-6-deoxy-6 -N-Boc-diamino-hexane-cyclomaltoheptaose

12 µl (0.049 mmole) of ditert.butyl bicarbonate are added at 0° C. and accompanied by stirring to 50 mg (0.041 mmole) of mono-6 -deoxy-6-diamino-hexane-cyclomaltoheptaose in 5 ml of DMF. Ambient temperature is restored, stirring takes place for 2 days and the solvent is eliminated under reduced pressure at 30° C. until an oil is obtained, which is treated with 75 ml of acetone. After one night at 4° C., the precipitate is isolated, washed with acetone and dried in vacuo at 30° C. This gives 46 mg (86%) of mono-6-deoxy-6-N-Boc-diamino-hexane-cyclomaltoheptaose.

MS: m/z =1333 [M+M]$^+$(M =1332 calc for $C_{53}H_{92}O_{36}N_2$);
IR:v =1665 cm$^{-1}$(NHCO);
RMN($^1$H, 500 MHz, D20), 5.05–5.20 ppm (H-1), 4.13 ppm (H-6A), 3.85–3.95 ppm (H-3), 3.65–3.74 ppm (H-2) 3.60–3.78 ppm (H-4), 3.41 ppm (H-4A), 4.29, 4.05, 3.95–3.75 and 3.63 ppm (H-5), 3.85 and 3.72 ppm (CH-a' and CH-b'), 3.24 ppm ($CH_2$-C), 2.97 and 2.91 ppm (CH-a" and CH-b"), 1.60 ppm ($CH_2$-d), 1.40 ppm ($CH_2$-e), 1.30 ppm (CH 2-f), 1.52 ppm (($CH_3$)$_3$).

EXAMPLE 2

Preparation of an inclusion complex of mono-6-deoxy-6-N-Boc-diamino-hexane-cyclomaltoheptaose and the sodium salt of anthraquinone sulphonic acid (ASANA)

The inclusion complex of ASANA is prepared by forming an aqueous solution including 6 mole/l of ASANA and 6 mole/l of mono-6-deoxy-6N-Boc-diamino -hexane-cyclomaltoheptaose. The solution is then examined by NMR spectro-metry of the proton at 500 MHz and at 298 K in $D_2O$. The spectrum obtained under these conditions is shown in FIGS. 1 and 2 (spectra 2 and 4). It is also possible to see the spectrum of cyclodextrin only of example 1 (spectrum 1) and ASANA only (spectrum 3).

In FIG. 1, spectrum 1 is the spectrum obtained with a 6 mole/l aqueous solution of the cyclodextrin derivative only.

On comparing spectra 1 and 2 of FIG. 1, it can be seen that the analysis of the chemical displacements of the different protons reveals a variation of the chemical displacements of protons H-3 and H-5 of the β-cyclodextrin modified by inclusion.

In FIG. 2 (spectrum 3) is shown the spectrum obtained with an aqueous solution containing only 6 mole/l of ASANA.

On comparing the two spectra 3 and 4, the displacement of the aromatic protons of ASANA reveals the inclusion thereof in the cavity of the cyclodextrin derivative.

EXAMPLE 3

Incorporation of the inclusion complex of example 2 in small unilamellar vesicles of dimyristoylphosphatidylcholine (DPMC)

A solution is prepared of ($CHCl_3$MeOH 85:15) 15 mM DMPC. The solvent is reduced under reduced pressure at 25° C., followed by the addition of 500 µl of water. Stirring takes place by means of a vortex in order to obtain a homogeneous suspension, followed by lyophilization. To the complex solution described in example 2 or to a 6 mmole/l solution of the cyclodextrin derivative only of example 1 is added the lyophilized DMPC. The substance then undergoes stirring, followed by sonication for 20 min until a transparent solution is obtained.

The solution is then examined by NMR spectrometry of $^{31}$P at 81 MHz. The spectrum obtained under these conditions is shown in FIG. 3 (spectrum 5).

Spectrum 6 is that obtained when using a 6 mmole/l solution of the cyclodextrin derivative only of example 1 in place of the solution of the inclusion complex of example 2 and spectrum 7 is that of the starting 15 mmole/l DMPC solution.

By comparing these spectra, it is possible to see that the inclusion of ASANA in the cavity of the cyclodextrin derivative favours the incorporation of the hydrophobic chain in small unilamellar vesicles of DMPC. These DMPC vesicles are biological membrane models. The incorporation of aliphatic chains of the cyclodextrin derivative leads to structures of the vesicular type covered with cyclodextrin cavities remaining on the outside, which can include in specific manner exogenous hydrophobic molecules.

Thus, the cyclodextrin derivatives according to the invention can be incorporated into small unilamellar vesicles of phospholipids, whilst retaining their hydrophobic molecule inclusion capacity.

We claim:
1. Cyclodextrin derivative according to formula:

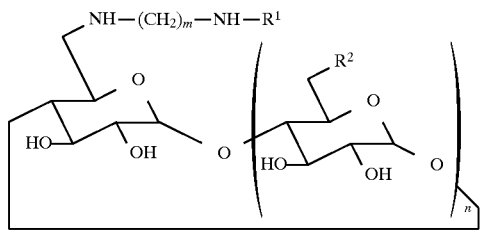

in which $R^1$ represents a group protecting an amine function, the $R^2$, which can be the same or different, represent OH or NH—$(CH_2)_m$—$NHR^1$, m is an integer from 2 to 18 and n is equal to 5, 6 or 7.

2. Cyclodextrin derivative according to claim 1, wherein $R^1$ is the nitrophenyl sulphenyl group, the fluoren-9-yl-methoxycarbonyl group, or a group of formula —$COOR^3$ in which $R^3$ is an alkyl group or an aryl group, optionally substituted.

3. Derivative according to claim 2, wherein $R^1$ is the t-butyl oxycarbonyl group.

4. Cyclodextrin derivative according to claim 3, wherein all the $R^2$ represent OH, n is equal to 6 and m is equal to 6.

5. Inclusion complex of a cyclodextrin derivative according to claim 4 with a hydrophobic chemical compound.

6. Cyclodextrin derivative according to claim 2, wherein all the $R^2$ represent OH.

7. Cyclodextrin derivative according to claim 2, wherein n is equal to 6.

8. Cyclodextrin derivative according to claim 2, wherein m is equal to 6.

9. Inclusion complex of a cyclodextrin derivative according to claim 2 with a hydrophobic chemical compound.

10. Organized surfactant system incorporating an inclusion complex according to claim 9.

11. System according to claim 10, wherein the surfactant is phospholipid.

12. Organized surfacant system incorprating a cyclodextrin derivative according to claim 2.

13. Cyclodextrin derivative according to claim 1, wherein all the $R^2$ represent OH.

14. Cyclodextrin derivative according to claim 1, wherein n is equal to 6.

15. Cyclodextrin derivative according to claim 1, wherein m is equal to 6.

16. Inclusion complex of a cyclodextrin according to claim 1 with a hydrophobic chemical compound.

17. Complex according to claim 9, wherein the hydrophobic chemical compound is pharmaceutically active molecule.

18. Complex according to claim 11, wherein the pharmaceutically active molecule is an anthracyclin.

19. Organized surfactant system incorporating an inclusion complex according to claim 9.

20. System according to claim 19, wherein the surfactant is a phospholipid.

21. Organized surfactant system incorporating a cyclodentrin dervative according to claim 1.

22. Process for the preparation of a cyclodextrin derivative according to the formula:

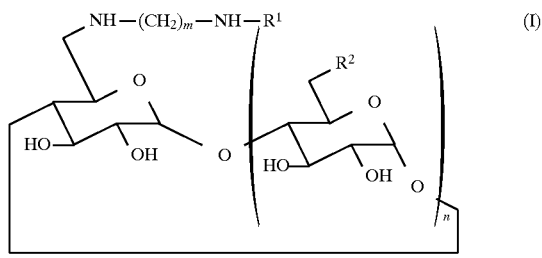

in which $R^1$ represents a group protecting an amine function, the $R^2$ represent OH, m is an integer from 2 to 18 and n is equal to 5, 6 or 7, wherein that it comprises the following stages:

a) reacting a cyclodextrin derivative of formula:

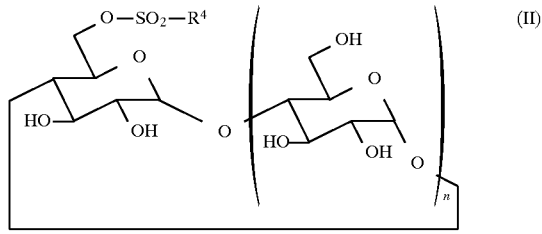

in which $R^4$ is a tosyl or naphthosulphonyl group, and n is equal to 5, 6 or 7, with a diaminoalkane of formula $NH_2$—$(CH_2)_mNH_2$, in which m has the meaning given hereinbefore, in order to obtain a cyclodextrin derivative of formula:

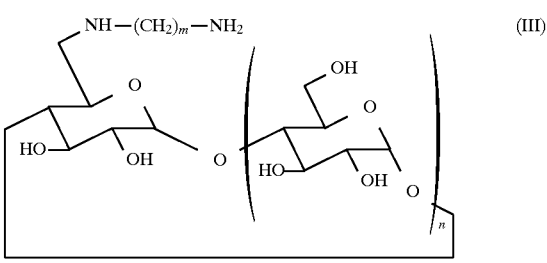

in which n and m are as defined hereinbefore and b) reacting the derivative of formula (III) with a reagent incorporating the protecting group $R^1$ to obtain the cyclodextrin derivative of formula (I).

23. Process for the preparation of a cyclodextrin derivative according to the formula:

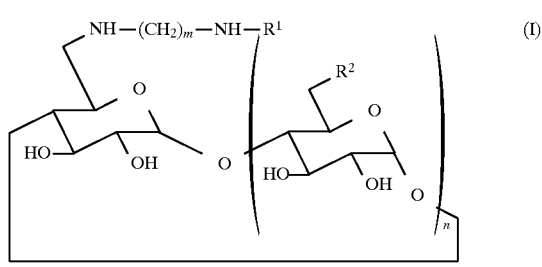

in which $R^1$ represents a group protecting an amine function is the nitrophenyl sulphenyl group, the flouren-9-methoxycarbonyl group, or a group of formula —$COOR^3$ in which $R^3$ is an alkyl group or an aryl group, optionally subsituted $R^2$ represents OH, m is an integer from 2 to 18 and n is equal to 5, 6 or 7, wherein the process comprises the following stages:

a) reacting a cyclodextrin dervative of formula:

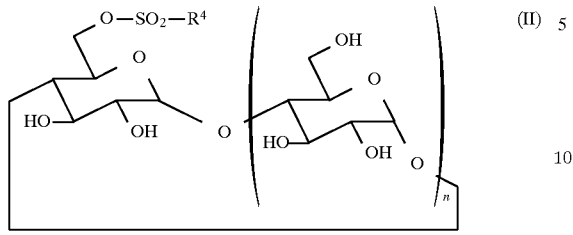

in which $R^4$ is a tosyl or naphthosulphonyl group, and n is equal to 5,6 or 7, with a diaminoalkane of formula $NH_2-(CH_2)_m-NH_2$, in which m has the meaning given hereinbefore, in order to obtain a cyclodextrin deruvative of formula:

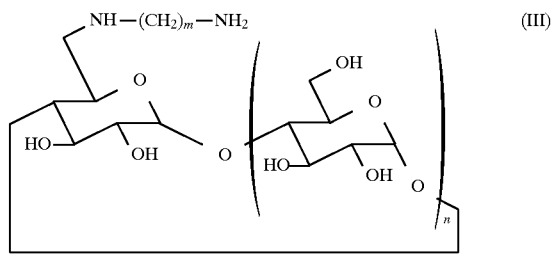

in which n and m are as defined hereinbefore and b) reacting the derivative of formula (III) with a reagent incorporating the above defined protecting group $R^1$ obtain the cyclodetrin dervative of formula (I).

* * * * *